United States Patent [19]

Inanaga et al.

[11] 4,088,755
[45] May 9, 1978

[54] MEDICAMENT FOR REMEDYING SCHIZOPHRENIA

[75] Inventors: Kazutoyo Inanaga, Kurume; Yoshio Miyamoto, Takarazuka, both of Japan

[73] Assignee: Takeda Chemical Industries, Ltd., Osaka, Japan

[21] Appl. No.: 689,144

[22] Filed: May 24, 1976

[30] Foreign Application Priority Data

May 23, 1975 United Kingdom ............... 22706/75

[51] Int. Cl.² ...................... A61K 31/54; A61K 37/00
[52] U.S. Cl. ...................................... 424/177; 424/247
[58] Field of Search ................................ 424/177, 247

[56] References Cited

U.S. PATENT DOCUMENTS 3,932,623   1/1976   Wilson ................................. 424/177

OTHER PUBLICATIONS

Medicinal Chemistry — Psychopharinaeological Agents, II—Gordon, pp. 50-52, 150-155, 316, 347, 380, 385, 398, 434-449.
Davis et al., Amer. Jour. of Psychiatry, vol. 132, No. 9, Sep. 1975, pp. 951-953.

Primary Examiner—Stanley J. Friedman
Attorney, Agent, or Firm—Wenderoth, Lind & Ponack

[57] ABSTRACT

The concomitant administration of L-pyroglutamyl-L-histidyl-L-prolinamide or its physiologically acceptable salt with one or more neuroleptics to patients suffering from schizophrenia can attain remarkable improvement of the overall disease picture of the patients.

9 Claims, No Drawings

MEDICAMENT FOR REMEDYING SCHIZOPHRENIA

The present invention relates to a medicament for remedying schizophrenia.

There are a variety of therapeutic methods which are currently used in the treatment of patients suffering from schizophrenia. These methods include psychotherapy, shock therapy, drug therapy and the like. Drugs used in such drug therapy are so called neuroleptics (called also antipsychotic drugs or major tranquilizers) such as phenothiazines, butyrophenones and thioxanthenes.

In schizophrenia, major symptoms are classified into two groups, namely fundamental symptoms and accessory symptoms; fundamental symptoms include associative disturbance, autism, affective incongruity and ambivalence, and accessory symptoms include hallucination, delusion, illusion, ideas of reference, depersonalization, negativism, antomatism, echolalia, echopraxia, mannerism, stereotypies, impulsiveness and "Benommenheit."

It has been recognized that neuroleptics currently used are effective in improving accessory symptoms, but at the same time, these drugs are very often not effective enough to cure fundamental symptoms and, thus fundamental symptoms are still marked after the introduction of medication with these neuroleptics. Furthermore, the improvement of symptoms by the administration of neuroleptics has been known to be reversible and symptoms once ameliorated tent to aggravate while the drugs are withdrawn. Therefore, many difficulties accompany the treatment of schizophrenia and novel medicaments which are more effective for the treatment have been long since desired.

L-Pyroglutamyl-L-histidyl-L-prolinamide (thyrotropin-releasing hormone; hereinafter referred to as TRH) is a hypothalamic hormone which can be synthesized chemically and has been used as a diagnostic agent or as an antidepressant. Its application to patients with schizophrenia has also been reported in, e.g. The Lancet, July 7, 1973, pages 43 and 44, to produce emotional warmth, lucidity of though and accessibility of psychotherapy. It is known, however, that, although the onset of the effect of TRH on psychotic patients is very rapid, the duration of its effects is rather short. Thus, TRH alone cannot be a practical remedy for psychotic patients.

We have found that the concomitant administration of TRH or its physiologically acceptable salts with conventional neuroleptic(s) to patients with schizophrenia results in an unexpectedly remarkable improvement of the overall disease picture of the patients, which can never be achieved by the administration of either TRH alone or these neuroleptic(s) alone, and this invention has been established on the basis of this finding.

Thus, the principal object of the present invention is to provide a method for the treatment of patients suffering from schizophrenia, which comprises administering to the patients TRH or a physiologically acceptable salt thereof and one or more neuroleptics. Another object of the present invention is to provide a pharmaceutical composition containing TRH or a physiologically acceptable salt thereof, and one or more neuroleptics, together with a pharmaceutically acceptable carrier therefor, which is usable for remedying schizophrenia. Other objects will be made clear from the description and claims hereinafter.

According to the present invention, the concomitant administration of TRH, or its physiologically acceptable salts, with neuroleptic(s) shows marked therapeutic effects on patients suffering from schizophrenia and the present invention is especially effective in treating patients whose main symptoms are the fundamental symptoms. Thus, by applying the present invention, even those patients with severe schizophrenia or with a long duration of illness, who show almost no responses to the therapies so far known, achieve a remarkable remission of symptoms to the extent that, in some cases, normal social life can be achieved.

In the following table, the effect of the concomitant use of TRH with chlorpromazine, a typical neuroleptic, on patients with schizophrenia is compared with that of chlorpromazine administration, the index being an improvement of the overall clinical picture.

|  | TRH-Chlorpromazine | Placebo-Chlorpromazine |
|---|---|---|
| Remarkable improvement | 4 | 1 |
| Moderate improvement | 1 | 0 |
| Slight improvement | 4 | 0 |
| Unchanged | 1 | 4 |
| Worsening | 1 | 2 |
| Total | 11 | 7 |

As shown in the table, in treating schizophrenic patients, tne combined use of TRH or its physiologically acceptable salts with neuroleptics achieves very remarkable effects, and thus, the present invention makes a significant contribution to the treatment of patients in this field.

The present inventors have observed a marked improvement of the overall clinical picture in schizophrenia by the concomitant use of L-3, 4-dihydroxyphenylalanine (hereinafter referred to as L-Dopa) in small doses with conventionally used neuroleptics, but this combined use has some limitation in clinical application, because an excessive does of L-Dopa results in the production of side-effects in the patients and therefore, the determination of the dose of L-Dopa is critical. On the other hand, according to the present invention, a deterioration of the patients considered to be caused by TRH in the combined use is negligible and, therefore, determination of the dose is very easy.

Furthermore, although the effect of TRH on pyschotic patients is known to be transient, t therapeutic effects in accordance with the present invention last long even after withdrawal of TRH or its physiologically acceptable salts, alone or together with neuroleptics, which are administered to patients in combination. In this way, long lasting therapeutic effects, as well as the rapid onset of the effects are another excellent characteristic of this invention.

For treating patients with severe schizophrenia, it is usual to administer various kinds of neuroleptics in a trial-and-error way but, according to the present invention, since only one or a few kinds of neuroleptics are enough to achieve therapeutic effects in combination with TRH or its physiologically acceptable salts, the number and dose of neuroleptics can be reduced and, therefore, the side-effects due to neuroleptics can be decreased remarkably.

As explained above, the medicament of this invention achieves very significant effects which cannpot be attained by medicaments so far known for the treatment of patients with schizophrenia.

Almost nothing is known about the mechanism of the valuable action of the combined use in accordance with the present invention. It can be assumed that fundamental symptoms, which cannot be cured with the administration of neuroleptics alone, are removed by the concomitant TRH. Alternatively, TRH may play the role of a trigger, making patients responsive to neuroleptics, which are ineffective without the introduction of TRH or its salts.

According to the present invention, TRH may be employed as the free base or in the form of a physiologically acceptable salt such as an acid addition salt e.g. a mineral acid salt (hydrochloride or sulphate, etc.), or an organic acid salt (acetate or tartrate, etc.). TRH tartrate (see Dutch Patent Application No. 7408881 laid open to public inspection) is especially convenient for the administration.

On the other hand, as neuroleptics in the present invention, all neuroleptics which are employable in the therapy of schizophrenia, can be used for the treatment. Representative neuroleptics are shown as follows:

a. Phenothiazines — Chlorpromazine, thioridazine, promazine, trifluoperazine, levomepromazine, thioproperazine, fluphenazine and perphenazine.

b. Butyrophenones — Haloperidol, trifluperidol, methylperidol, benzoperidol, spiroperidol, pimozide, fluspirilene, and penfluridol.

c. Thioxanthenes — Thiothixene, chlorprothixene and flupentixol.

d. Dibenzothiazepines — Clotiapine.

e. Carpipramines — Carpipramine and clocapramine.

In the present invention, TRH or its physiologically acceptable salt is administered to patients suffering from schizophrenia in combination with one or more of the above-mentioned neuroleptics. The administration route and the dose are determined depending on the kind and severity of the patient's symptoms. Generally, however, the advantageous dose of TRH, or its salts, in oral routes is about 0.5 to 50 mg in terms of free TRH/adult patient/day, more particularly about 1 to 10 mg in terms of free TRH/adult patient/day and, when intravenously or intramuscularly administered, the advantageous dose is about 10 to 1000 μg in terms of free TRH/adult patient/day, more particularly about 50 to 700 μg in terms of free TRH/adult patient/day. The dosage of neuroleptics may be a usual one for the conventional sole use of the respective neuroleptics and generally chosen within the following range:

a. Phenothiazines; orally — about 30 to 300 mg/adult patient/day, intravenously or intramuscularly — about 1 to 250 mg/adult patient/day.

b. Butyrophenones; orally — about 0.5 to 150 mg./adult patient/day, intravenously or intramuscularly — about 2.5 to 75 mg./adult patient/day.

c. Thioxanthenes; orally — about 10 to 200 mg./adult patient/day, intravenously or intramuscularly — about 30 to 60 mg./adult patient/day.

d. Dibenzothiazepines; orally — about 60 to 120 mg./adult patient/day, intravenously or intramuscularly — about 30 to 50 mg./adult patient/day.

e. Carpipramines orally — about 30 to 300 mg./adult patient/day.

In the present invention, to patients with schizophrenia, TRH or its physiologically acceptable salts and neuroleptics can be administered either as one pharmaceutical composition or separately. The pharmaceutical composition containing TRH or its physiologically acceptable salts together with one or more neuroleptics may be in any form of such pharmaceutical preparations as powders, granules, tablets, capsules, troches, drops, solutions, injections, emulsions, syrups, elixirs, etc. These preparations can be produced in per se known manner as with the usual pharmaceutical preparations. Carriers are chosen depending on the administration routes or the solubility of the neuroleptics used.

The following clinical data as well as Examples are only for illustrative purposes and are not at all intended to limit or to restrict the scope of the invention.

Case 1. A 37-year-old male

At the end of March, 1974, the patient met a traffic accident and began to show talkativeness and insominia. On around April 10, the patient began to have a feeling of being attacked and showed an inability to think goal-directedly and to sleep. On April 14, he came back to his home town and, on the following day, was admitted to hospital. At the time of his hospitalization, there were auditory hallucinations, delusions of reference and persecution, idea of observation, autism, affective stiffness, indifference, mutism, dull movement and awkward behaviour.

With hospitalization, thioridazine 100 mg. per day, spiperone 1.0 mg. per day and trihexyphenidyl 8 mg. per day were started to be administered. At the end of April, the patient showed an almost complete disappearance of delusions and fairly good responses but the feeling of being attacked remained unchanged and his face was still stiff and expressionless. At the same time, an irritation began to appear occasionally, and thioridazine 100 mg. per day was used for the treatment. From May 8, in addition to thioridazine, penfluridol 20 mg. was administered once a week.

On May 14, the feeling of being attacked disappeared and the response became very vivid. Contact with others was improved but the stiff facial expression and awkward behaviour were still observed.

From the same day, thioridazine 50 mg. per day and penfluridol 30 mg. per week were started to be administered and on May 21, the administration of thioridazine was stopped. The dose of penfluridol was increased to 35 mg. per week on May 29 and to 40 mg. per week on June 5. Abnormal experiences were not observed at all and the stiffness of facial expression and awkwardness in behaviour were the only symptoms of the patient.

On June 6, when the patient was allowed to visit his home, anxiety began to appear on the train on his way home. On June 10, when he returned to the hospital, the patient showed anxiety and a feeling of being attacked was observed. He could not stay still and showed a stiff facial expression and awkward behaviour. On the same day, thioridazine 50 mg. per day was added to the regime again. From June 17, the feeling of instability was removed but he was devoid of cheerfulness and complained of a lack of energy. No improvement was observed in facial expression and behaviour and at the same time, tremors of the fingers began to occur and trihexyphenidyl 6 mg. per day was added to the regime. On June 21, the tremors disappeared but the other symptoms remained unchanged and penfluridol was reduced to 30 mg. per week. On July 2, the stiffness of facial expression was removed a little and irritability disappeared completely, but at the same time, abulia began to appear and, on July 3, the administration of penfluridol was stopped.

On July 10, TRH tartrate monohydrate 4 mg. (2.73 mg. in terms of free TRH) per day (2 mg. each in the morning and night) began to be administered orally in combination with thioridazine, 50 mg. per day, and trihexyphenydyl 6 mg. per day. Before the initiation of the TRH therapy, the patient showed remarkable autism and abulia together with facial stiffness, slow movement and awkward behaviour. On July 12 the facial expression became a little softer and the facial movement was improved. On July 20, the stiffness as a whole was removed, the emotional expression was clear and the behaviour was active. Contact with others and spontaniety were improved. The symptoms showed increasing recovery and on July 29, insight began to appear and expression and behaviour became very cheerful and active. On July 31, the administration of TRH was stopped.

The administration of the other drugs was continued after the withdrawal of TRH. From August 2 to 6, the patient was allowed to leave the hospital. His state of remission has been maintained until now.

Case 2. A 39-year-old male

In February 1961, the patient was admitted for the first time to Y hospital in a state of catatonic stupor. After receiving electroshock therapy and chlorpromazine, he was discharged from the hospital on April 19 of the same year. On May 26, 1966 he was again admitted to the same hospital this time in a state of catatonic excitement. After hospitalization, he received insulin shock therapy conjoined with chlorpromazine and thioridazine, but without any significant improvement. Since the middle of 1970, treading and bizarre oral movements (mumbling) became prominent. While in hospital he appeared to have hallucinations, a delusion of reference and a delusion of persecution. Beginning on April 3, 1971, thioridazine, 300 mg. per day, and L-Dopa, 400 mg. daily, were added to the therapeutic regime. One week later, his hitherto vacant facial expression began to show something solid. The mumbling and treading became reduced and hallucinations and delusions seemed diminishing. From the 9th day on, the dosage of L-Dopa was increased to 600 mg. daily. At the 2nd week he appeared free from hallucinations but was still inactive. At the 3rd week he began to be more active than before and was able to participate in an exercise or occupational therapy program. His delusions also phased out, not bothering him any more. At the 6th week of this combined therapeutic regime with L-Dopa, the patient was willing to take part in work outdoors; his expression became more vivid than before. In the 10th week his incongruous laughter was markedly reduced and he even began to criticise his delusions and hallucinations. At the 12th week the dosage of thioridazine was reduced to 125 mg. daily and further to 100 mg. from the 14th week; his scepticism toward his morbid experience now became more evident. At the 19th week, the dosage of L-Dopa was reduced to 400 mg. and the drug was discontinued that week-end. The patient then was still somewhat autistic and close-mouthed, but had no morbid experience and appeared to have a clear insight.

As he remained symptom-free while on thioridazine, 75 mg. daily after stoppage of L-Dopa, he was discharged from the hospital on Sept. 1, 1971. However, in mid-December he again developed hypochondriacal delusions of increasing severity with associated auditory hallucinations and began to refuse eating. Autism and abulia were quite prominent and his face became entirely expressionless. With these symptoms he was admitted to Y hospital for the third time on Dec. 20, 1971.

At the time of this hospitalization, there were intense negativism, auditory hallucinations and delusions of reference and persecution with concurrent psychomotor excitement and marked degrees of autism, apathy and mutism.

Hospital therapy was started with chlorpromazine, 400 mg. per day, and spiperone, 1 mg. per day. With this regimen, his negativism and psychomotor excitement seemed to disappear almost completely. However, other symptoms remained virtually unaffected. Towards June 16, 1972, auditory hallucinations again became intense and the patient fell in an agitated state. Consequently, the dosage of chlorpromazine was raised to 500 mg. per day. Several days later, the hallucinations were somewhat reduced and his agitated state seemed to have gone. Beginning on August 9, penfluridol, 20 to 40 mg. twice weekly, was added to the preceding regimen of chlorpromazine 500 mg. daily. On June 26, 1973, the dosage of chlorpromazine was reduced to 200 mg. per day. Shortly thereafter, L-Dopa, 100 mg. daily, was added to the regimen from July 5 on. The dosage of L-Dopa was then increased gradually up to 600 mg. per day and finally discontinued on August 30.

With L-Dopa therapy there was an improvement in his ability to communicate with others; he looked somewhat softened but was still expressionless. Autism and abulia persisted. His general clinical picture improved to a considerable extent, however. On July 2, 1974, he was started on clocapramine, 75 mg. daily, to which TRH tartrate monohydrate, 4 mg. (2.73 mg. in terms of free TRH) daily, was orally added from July 29 on. At the outset of TRH medication, he could respond fairly well to verbal commands, but would not speak spontaneously to others, giggled in an inappropriate way and his face was somewhat rigid and poor in expression. Generally, there was a lack of energy in him and little contact with others. Abulia was prominent. He also retained the idea of observation and had tremors of the fingers and of the tongue. From August 2 onwards, trihexyphenidyl, 6 mg. per day, was added to the regimen. On August 5 (the 8th day after initiating TRH therapy), the tremors were far less marked and he became more active and more vivid in his facial expression than before. He verbalised that his feeling of being observed by others had gone somewhere. Toward August 10, he said "I am feeling much better now and I want to do something". His inappropriate laughter was also markedly reduced. On August 16, he could speak spontaneously and stated; "My feeling of being withdrawn is gone and I feel light-hearted". Also he said; "I feel like giving it a try with exercise and doing some work". During interview, he was polite and cordial. He continued to be in a similar improved condition for subsequent days and as such was withdrawn from TRH on August 18. Since then, he has been on clocapramine, 75 mg. daily, alone for 4 months, during which remission has been maintained most of the time.

Case 3. A 42-year-old male

From April, 1953 (when attending a certain university) he complained that his hair roots became strange owing to low back pain and he had to pull some hair on some occasions and felt his face got twisted or something. He would also say that he felt his existence was meaningless; even in his boarding room, he was not relaxed, didn't sleep at night and roamed about his room. Because of these behavioural abnormalities, the patient was recalled home, whereupon he consulted with the neuropsychiatric clinic of a medical school hospital, and was diagnosed as suffering from schizophrenia and admitted to a mental hospital. After 5 months, he was reasonably free from symptoms and discharged from the hospital. After that, he went back to university, graduated from there, and worked as a teacher at a junior high school. One month after getting his job, he began to have monologia, auditory hallucinations and delusion of persecution, and frequently stayed away from school, saying that his pupils and colleagues were making a fool of him and had evil designs upon him. After two months, he left his school and stayed at home. Monologia and inappropriate giggling were then conspicuous and their intensity gradually increased. His behavioural abnormalities continued to increase culminating in occasional impulsive acts.

With these symptoms, he was admitted to a mental hospital in September, 1955 and was discharged from the hospital in February of the following year. Later, on May 23, 1958, he was admitted to S hospital. At the time of hospitalization, his presenting symptoms were hallucinations, delusions, insomnia, monologia, incongruous laughter, emotional poverty, diminished spontaneity, disturbed affective rapport and vacant facial expression. After hospitalization, he received electroshock treatment (hereinafter referred to as E.C.T.), insulin shock therapy and medication with multiple antipsychotic drugs. Following E.C.T., some symptomatic improvement was observed during the initial 1 to 2 weeks but exacerbation occurred before long. The drug effect was more or less the same with any of the antipsychotic drugs used. While on drug therapy, hallucinations, delusions, inappropriate laughter and monologia became no longer discernible, whereas a dulled affect, decreased spontaneity, abulia and autism gradually intensified. During his hospital stay, he went out of his room only infrequently, remaining in bed most of the time or sitting on a chair with his eyes closed. During the period of May to July, 1971, L-Dopa was used concomitantly with 300 mg. per day chlorpromazine. The dosage was 200 mg. initially and was then increased stepwise by increments of 100 mg. at weekly intervals up to a maximum of 1200 mg. At the end of the 3rd week after initiating the L-Dopa treatment (dosage then was 400 mg.), there was an appreciable improvement in his facial expression (his facial expression became natural and he could cheer up), his plunted affect was improved and some degree of spontaneity was manifest.

However, while on L-Dopa at 1000 mg. daily, he seemed irritated to some extent and complained of sleeping trouble. The use of L-Dopa at 1200 mg. was associated with the appearance of auditory hallucination, leading to discontinuation of the drug. One week after the cessation of the L-Dopa treatment the irritability, insomnia and hallucination has disappeared. Later, during the period from November 1971 to March 1972, L-Dopa, 200 to 600 mg. daily, was administered again concomitantly with thioridazine, 200 mg. daily. While on L-Dopa at 300 mg. daily his spontaneity increased to an extent greater than that achieved before and his blunted affect and disturbed affective rapport were improved. The patient was now willing to participate in occupational or recreational therapy. After about 5 months of usage, L-Dopa was withdrawn. During a subsequent period of about 4 months, his condition remained the same as with L-Dopa. Thereafter, there was a gradual return to the state prior to the initiation of L-Dopa. This case may thus be categorized as having responded quite favourably to L-Dopa. Later, on July 7, 1974, therapy was resumed with oral administration of thioridazine, 200 mg. daily, and TRH tartrate monohydrate, 8 mg. daily (5.46 mg. in terms of free TRH; given in two divided doses, morning and evening) and continued for two weeks. At the start of this therapy, the patient showed reduced spontaneity, dulled affect, lack of insight and disturbance of affective rapport. As a matter of fact, paucity of reality in the content of his speech was evident and there was some difficulty in making a thorough contact with him. However, on the 3rd day of instituting TRH he said: "I feel myself like buoyant now and with a clear head, I can think of things very smoothly, and I can enjoy eating."

On the 4th day he said: "Due to my long hospitalization, it is difficult to get back to my work as a teacher and I am considering working as a farmer." The contents of his talks thus showed a changing tendency to reality-related affairs. His facial expression was quite different from what it was previous to TRH therapy, he was active and talked to the physician while looking at his eyes. Up until that time, he was wearing work clothing but at sleeping time, he began changing to pyjamas and, in the morning, replacing his pyjamas with pants and a shirt. Also, his heretofore ignored possessions around the bed were well aligned. His participation in work and recreational activities became more positive and his action became more agile than when he was placed on L-Dopa.

He showed a willingness to accept occupational or recreational therapy, was more energetic than when he was on L-Dopa and also showed an intensified interest in newspapers and television. Thus, he began to show an interest in society. The patient is now withdrawn from TRH and is being given thioridazine alone. The effect of TRH therapy has persisted for two months after its discontinuation.

Case 4. A 24-year-old female

In this patient, the onset of disease presumably was in May, 1971. On Oct. 8, 1971, she was admitted to a mental hospital under the diagnosis of schizophrenia and stayed there until December 2 of the next year. Her presenting symptoms at the time of her first institutionalization were absent-mindedness while at work, diminution of working ability, mutism and autistic manifestations. After treatment, she was reasonably free from the symptoms and discharged from the hospital. Later, on Feb. 20, 1974, she was again admitted to K university hospital, this time in a stuporous state. E.C.T. was given at a frequency of four times per week. Toward the 8th day of initiating the therapy, the patient was spending all day sitting in her bed with her face turned downwards. She was able to take care of her discharge, but during examinations or interview she was close-mouthed and even refused to answer questions. At that time, catalepsy became evident. Likewise, she showed a strong tendency to refuse to eat and had therefore to be assisted in this routine chore. During these periods, she was on chlorpromazine, 25 mg. daily, given by injection in two divided doses, morning and evening. In a matter of two weeks, her mutism and negativism were improved to some extent, but still she would not answer questions about her morbid experience. As her condition improved to the point of accepting oral mediciation, chlorpromazine was given at an initial dosage of 100 mg. daily and then on a gradually increasing dose basis, but without result. Haloperidol was tried then. The dosage was 4 mg. daily initially and was increased up to 100 mg. thereafter. This therapy, too, failed to elicit any appreciable symptomatic response. Later on, her affect became blunted, she looked expressionless and would just obey the nursing staff's orders. Again, she fell into a substuporous state, which made it necessary to have recourse to E.C.T. For several days following E.C.T., she was fairly well and it was not necessary for her to seek the aid of nursing staff in her activities of daily living. Shortly thereafter, a worsening of her symptoms occurred: negativism, mutism, autism and a dulling of affect became conspicuous. In those days, psychotic episodes and subsequent drug therapy thus repeated themselves. On June 15, she became stuporous again. After E.C.T. was given twice, she was rid of her stupor. She was capable of doing the activities of daily living, but the above-mentioned psychotic symptoms still remained unimproved. At the time, she was on a regimen of haloperidol, 12 mg. daily, and diazepam, 9 mg. daily.

On June 21, the patient was started on TRH. TRH tartrate monohydrate was given for 14 days at 4 mg. (2.73 mg. in terms of free TRH) daily while other concomitant drugs were obtained on the same dosage schedule as before. At the 4th day after initiating the TRH therapy, a marked improvement occured in her facial expression; she behaved politely toward the physician, nursing staff and inmates, and the quality and amount of her talks became evidently solidified. In her inmates' bed she sang, read magazines and watched TV, thus showing a definite behavioural improvement. She also confessed to having had auditory hallucinations.

Case 5. A 22-year-old female

In November 14, 1973, the patient was admitted for the first time to H hospital. Before the onset of the illness, she was an introvert, being taciturn, gentle and shy.

From the beginning of September 1973, she began to complain of insomnia gradually and say "My face is strange (my forehead is too broad) and others are laughing at me for that. I don't want to do anything" and then stopped working. At the same time of her institutionalization, she showed delusion of reference, insomnia and lacked insight. A vacant facial expression and a lack of spontaneity were recognized, and she complained of an inability to think goal-directedly and responded to the doctor with her face turning downwards and a weak voice. She could answer to questions only in a simple way with a little interval after she was questioned.

After hospitalization, the drugs used for therapy were haloperidol, thioridazine, diazepam, chlorpromazine and so on, which were administered at the doctor's discretion. At the beginning of December, 1973, she showed a suicidal tendency, which disappeared after use 5 times of E.C.T. At the end of February 1974, her abnormal experiences disappeared, but she was devoid of vivid facial expression and spontaneity and could not take care of herself before she was asked to do so. Since then, many remedies were tried, including the combined use of drugs such as chlorpromazine-propericiazine, chlorpromazine-perphenazine and thioridazine-perphenazine, but no changes of the symptoms were observed.

Before the initiation of TRH therapy, the patient had no abnormal experiences, but she could show only a weak response and didn't talk from her side at all. She was able to wear her clothes, wash her face and eat by herself and participate in work but her efficiency was very low. After confirming that the patient was euthyroid ($T_4$: 4.8 $\mu g/d\lambda$), on July 14, 1974, TRH tartrate monohydrate 4 mg. (2.73 mg. in terms of free TRH) daily was added to the regimen and was administered in two divided oral doses, after meals, morning and evening. In the afternoon of the second day after initiation of the TRH therapy, her facial expression became fairly soft, and on the third day she was allowed to go home on trial. At this time, her expression became very cheerful and she spoke to her family about the hospital actively, though she had not done so before. When neighbours and relatives visited her, she had used to hide in a corner of the room but, this time, she could greet and talk to others and help her family actively. On the 5th day after the initiation of the TRH therapy, the doctor recognized that her facial expression was soft and clear and she could reply very clearly to the doctor, looking the doctor in the face. She felt free from a depressed feeling and pleasant. When she returned to the hospital again, the patients roomed together with her were surprised that she greeted them. Soon after she visited her home, her mother cam to the hospital and explained her above state with surprise. She began to participate in work actively and her behaviour became much more active than before. TRH therapy was stopped on the 15th day from the initiation, but the improvement has continued even after withdrawal of TRH. She clearly denied abnormal experiences and began to make her toilet.

The doctor admitted that the patient was well enough to leave hospital and the patient was discharged from the hospital on August 17, 1974. Since then, observation has been continued on the patient but no change in the improved state has been observed until today (January 1975).

Case 6. A 48-year-old female

At the onset of schizophrenia, she was admitted to the hospital in fall, 1970. At the time of her hospitalization, the main symptoms were hallucination, delusion and psychomotor excitement. She received the conventional drug therapies, made recovery from the disease and was allowed to leave the hospital. In December of 1971, she had a relapse of the disease and was admitted again to the hospital and, although hallucination and delusion disappeared within 2 months, her depressive and pessimistic feeling was left unimproved by the known therapies and she was in devoid of spontaineity and continued to keep her bed with abulia. Psychotic symptoms such as insomnia, anorexia, headache, etc. appeared now and then and ideas of reference and ideas of observation continued to a slight extent. These symptoms did not repond to various drug therapies tried.

On June 14, 1974 she began to receive intravenous injections of TRH (730 $\mu$g. TRH tartrate monohydrate (500 $\mu$g in terms of free TRH)/day). One hour after the first injection, she told, "I am feeling very light in the head and free from depressed feeling." The ameliorated state continued ever since and she was active and did not show the psychotic symptoms any longer after this. Remarkable improvement in the symptoms was recognized subjectively as well as objectively, only with infrequent incidence of insomnia. TRH was injected once every 2 or 3 days and she received 5 injections totally. During the TRH therapy, perphenazine (12 mg./day), diazepam (10 mg./day), vegetamim B (1 tablet/day) were concomitantly administered. One month after the termination of the TRH therapy, there appeared termporal insomnia and delusion of reference, which disappeared after a week. This case showed the effectiveness of combined administration of TRH with the neuroleptics to the amelioration of schizophrenia, which had lasted for 2 and a half years.

Examples

Some examples of practical recipes in which TRH or its physiologically acceptable salts and neuroleptics are utilized as remedies for schizophrenia are as follows:

| Example 1 (Tablet) | | |
|---|---|---|
| (1) TRH tartrate monohydrate | 2.0 | mg. |
| (2) Haloperidol | 1.5 | mg. |
| (3) Lactose | 51.5 | mg. |
| (4) Corn starch | 150 | mg. |
| (5) Microcrystalline cellulose | 30 | mg. |
| (6) Magnesium stearate | 5 | mg. |
| | 240 | mg. per tablet |

Components (1), (2), (3) and (4), 2/3rds the quantity of component (5) and one-half the quantity of component (6) are thoroughly mixed, and then the mixture is granulated. The remaining ⅓rd quantity of component (5) and one-half component (6) are added to the granules and compressed into tablets. The prepared tablets can further be coated with a suitable coating agent, e.g. sugar.

| Example 2 (Capsule) | | |
|---|---|---|
| (1) TRH tartrate monohydrate | 2.0 | mg. |
| (2) Thiotixene | 10 | mg. |
| (3) Lactose | 110 | mg. |
| (4) Microcrystalline cellulose | 70 | mg. |
| (5) Magnesium stearate | 8 | mg. |
| | 200 | mg. per capsule |

Components (1), (2), (3) and (4) and one-half the quantity of component (5) are thoroughly mixed, and then the mixture is granulated. The remaining one-half of component (5) is added to the granules and the whole is filled into a gelatin capsule.

| Example 3 (Injection) | |
|---|---|
| (1) TRH tartrate monohydrate | 500 µg. |
| (2) Chlorpromazine | 10 mg. |
| (3) Inositol | 100 mg. |

| -continued | |
|---|---|
| Example 3 (Injection) | |
| (4) Benzyl alcohol | 20 mg. |

All the ingredients are dissolved in water to make 2.0 mλ of the solution (pH 4.0 to 5.0) serving as an injection.

What is claimed is:

1. A method for the treatment of a patient suffering from schizophrenia, which comprises administering to said patient an effective amount of L-pyroglutamyl-L-histidyl-L-prolinamide or a physiologically acceptable salt thereof and a phenothiazine neuroleptic agent selected from the group consisting of chlorpromazine, thioridazine, promazine, trifluoperazine, levomepromazine, thioproperazine, fluphenazine and perphenazine, the weight ratio to L-pyroglutamyl-L-histidyl-L-prolinamide or a physiologically acceptable salt thereof in terms of free L-pyroglutamyl-L-histidyl-L-prolinamide to the phenothiazine neuroleptic agent being from 1:25000 to 50:30.

2. A method as claimed in claim 1 wherein L-pyroglutamyl-L-histidyl-L-prolinamide or a physiologically acceptable salt thereof is administered parenterally or orally together with the phenothiazine neuroleptic agent.

3. A method as claimed in claim 2 wherein L-pyroglutamyl-L-histidyl-L-prolinamide or a physiologically acceptable salt thereof is administered orally in an amount of about 0.5 to 50 mg. in terms of free L-pyroglutamyl-L-histidyl-L-prolinamide per adult patient per day.

4. A method as claimed in claim 2 wherein L-pyroglutamyl-L-histidyl-L-prolinamide or a physiologically acceptable salt thereof is administered intravenously in an amount of about 10 to 1,000 µg. in terms of free L-pyroglutamyl-L-histidyl-L-prolinamide per adult patient per day.

5. A method as claimed in claim 1 wherein the physiologically acceptable salt is the tartrate.

6. A pharmaceutical composition for the treatment of a patient suffering from schizophrenia, which comprises an effective amount of L-pyroglutamyl-L-histidyl-L-prolinamide or a physiologically acceptable salt thereof and a phenothiazine neuroleptic agent selected from the group consisting of chlorpromazine, thioridazine, promazine, trifluoperazine, levomepromazine, thioproperazine, fluphenazine and perphenazine, the weight ratio to L-pyroglutamyl-L-histidyl-L-prolinamide or a physiologically acceptable salt thereof in terms of free L-pyroglutamyl-L-histidyl-L-prolinamide to the phenothiazine neuroleptic agent being from 1:25000 to 50:30.

7. A composition as claimed in claim 6, which is in the form of oral preparation.

8. A composition as claimed in claim 6 which is in the form of injectable solution.

9. A composition as claimed in claim 6 wherein the physiologically acceptable salt is tartrate.

* * * * *